(12) United States Patent
Lewandowski et al.

(10) Patent No.: US 6,599,269 B1
(45) Date of Patent: Jul. 29, 2003

(54) SINGLE-USE SYRINGE

(75) Inventors: Raymond D. Lewandowski, New Providence, NJ (US); Karin Gunther, Fort Lee, NJ (US); Marcos Calucho Villas, Huesca (ES)

(73) Assignee: Becton Dickinson and Company, Franklin Lakes, NJ (US)

( * ) Notice: Subject to any disclaimer, the term of this patent is extended or adjusted under 35 U.S.C. 154(b) by 206 days.

(21) Appl. No.: 09/631,362

(22) Filed: Aug. 2, 2000

(51) Int. Cl.⁷ .................................. A61M 5/00
(52) U.S. Cl. .................... 604/110; 604/192; 604/195; 604/210
(58) Field of Search ................... 604/110, 192, 604/195, 198, 209, 210, 219, 230, 220

(56) References Cited

U.S. PATENT DOCUMENTS

| | | | |
|---|---|---|---|
| 2,158,593 A | 5/1939 | Scrimgeour | 128/221 |
| 2,902,995 A | 9/1959 | Loper | 128/215 |
| 3,179,107 A | 4/1965 | Clark | 128/221 |
| 3,234,944 A | 2/1966 | Stevens et al. | 128/221 |
| 3,320,954 A | 5/1967 | Cowley | 128/218 |
| 4,027,669 A | 6/1977 | Johnston et al. | 128/218 |
| 4,430,080 A | 2/1984 | Pasquini et al. | 604/240 |
| 4,676,530 A | 6/1987 | Nordgren et al. | 285/93 |
| 4,775,363 A | 10/1988 | Sandsdalen | 604/110 |
| 4,863,427 A | 9/1989 | Cocchi | 604/110 |
| 4,919,652 A | 4/1990 | Alter et al. | |
| 4,950,240 A | 8/1990 | Greenwood et al. | 604/110 |
| 4,973,310 A | 11/1990 | Kosinski | |
| 5,000,735 A | 3/1991 | Whelan | 604/110 |
| 5,004,460 A | 4/1991 | Gimeno | 604/228 |
| 5,149,323 A | 9/1992 | Colonna | 604/110 |
| 5,181,912 A | 1/1993 | Hammett | 604/110 |
| 5,201,709 A | 4/1993 | Capra et al. | 604/110 |
| 5,205,833 A | 4/1993 | Harsh et al. | 604/240 |
| 5,215,524 A | 6/1993 | Vallelunga et al. | 604/110 |
| 5,226,882 A | 7/1993 | Bates | 604/110 |
| 5,242,401 A | 9/1993 | Colsky | 604/110 |
| 5,318,536 A * | 6/1994 | Williams | 604/110 |
| 5,336,200 A | 8/1994 | Streck et al. | 604/198 |
| 5,383,857 A | 1/1995 | Levitov | 604/110 |
| 5,403,286 A * | 4/1995 | Lockwood, Jr. | 600/576 |
| 5,489,272 A | 2/1996 | Wirtz | 604/110 |

(List continued on next page.)

FOREIGN PATENT DOCUMENTS

| | | |
|---|---|---|
| DE | 2939180 C2 | 4/1980 |
| EP | 0 037 920 A1 | 10/1981 |
| EP | 0 047 042 A2 | 3/1982 |
| EP | 0 364 777 | 4/1990 |
| GB | 1 286 690 | 12/1969 |
| GB | 2214 082 A | 8/1989 |
| GB | 2 256 146 A | 12/1992 |
| GB | 2 318 060 A | 4/1998 |
| WO | WO 95/23005 | 8/1975 |
| WO | WO 89/10766 | 5/1988 |
| WO | WO 96/30076 | 10/1996 |
| WO | WO 97/31665 | 9/1997 |

Primary Examiner—Thomas Denion
Assistant Examiner—Jaime Corrigan
(74) Attorney, Agent, or Firm—Jeanne P. Lukasavage

(57) ABSTRACT

A syringe assembly includes a barrel having a chamber for retaining fluid. The barrel has an open proximal end, a distal end and an elongated tip extending from the distal end having a passageway therethrough in fluid communication with the chamber. The tip has a diameter at its distal end of less than about 3.8 mm and a side wall tapered proximally outwardly at a taper of from 4% to 8%. A plunger rod includes an elongated body portion having a proximal end, a distal end and a stopper at the distal end. The stopper is slidably positioned in fluid-tight engagement in the barrel. An elongated projection extending distally from the distal end of the plunger rod is shaped to fit within the passageway of the elongated tip. Structure is provided for preventing proximal motion of the plunger rod with respect to the barrel after distal motion of the stopper to expel fluid through the passageway.

28 Claims, 16 Drawing Sheets

U.S. PATENT DOCUMENTS

| | | |
|---|---|---|
| 5,605,544 A | 2/1997 | Tsao .......................... 604/110 |
| 5,643,211 A | 7/1997 | Sadowski et al. ........... 604/110 |
| 5,697,917 A | 12/1997 | Sadowski et al. ........... 604/218 |
| 5,738,655 A | 4/1998 | Vallelunga et al. ......... 604/110 |
| 5,769,822 A | 6/1998 | McGary et al. ............. 604/110 |
| 5,833,660 A | 11/1998 | Nathan et al. .............. 604/110 |
| 6,013,056 A | 1/2000 | Pettersen ................... 604/110 |
| 6,206,856 B1 * | 3/2001 | Mahurkar ................... 604/110 |

* cited by examiner

SINGLE-USE SYRINGE

BACKGROUND OF THE INVENTION

1. Field of the Invention

The present invention relates to syringes and needles and more particularly concerns disposable syringes and needles having re-use prevention and medication saving features.

2. Background

Throughout the world the multiple use of hypodermic syringe products, which are intended for single use only, is instrumental in drug abuse and in the transfer of contagious diseases. Intravenous drug users who routinely share and re-use syringes are a high risk group with respect to the AIDS virus. Also, the effects of multiple use are a major concern in some countries where repeated use of syringe products during mass immunization programs may be responsible for the spread of many diseases. Re-use of single use hypodermic syringe assemblies is also instrumental in the spread of drug abuse even in the absence of infection or disease.

Many attempts have been made to remedy this problem. Most notable are early contributions which relied on a specific act to destroy the syringe after use either by using a destructive device or providing a syringe assembly with frangible zones so that the syringe could be rendered inoperable by the application of force. Other attempts involve the inclusion of structure which would allow the destruction or defeating of the syringe function through a conscious act by the syringe user. Although many of these devices work quite well they do require the specific intent of the user followed by the actual act to destroy or render the syringe inoperable. These devices are not effective with a user having the specific intent to re-use the hypodermic syringe. Accordingly, there is a need for a single use hypodermic syringe which becomes inoperative or incapable of further use automatically without any additional act on the part of the user. This automatic function is much harder to provide because the means for rendering the syringe inoperable must not prevent its filling or use under normal conditions.

In single-use syringes using needle assemblies having a hub attached to a needle cannula there is a need to help prevent reuse of the needle assembly after its use with the single-use syringe so that the needle assembly cannot be used again with other syringes or fluid handling devices.

There is also a need in single-use syringes to minimize or eliminate wasted medication in the injection process. This is especially true in mass inoculation programs involving large numbers of people and in many cases limited financial resources. Medication which is not delivered, because it is trapped in the interior of the syringe tip after the plunger reaches its maximum distal displacement, can prove costly. Even with a small number of injections, an entire dose may be lost through medication which is trapped in the syringes and not delivered.

SUMMARY OF THE INVENTION n operable syringe assembly includes a barrel having an inside surface describing a chamber for retaining fluid. The barrel includes an open proximal end, a distal end and an elongated tip extending from the distal end having a passageway therethrough in fluid communication with the chamber. The tip has a side wall tapered proximally outwardly at a taper of from 4% to 8%. A plunger rod includes an elongated body portion having a proximal end, a distal end and a stopper at the distal end. The stopper is slidably positioned in fluid-tight engagement in the barrel. An elongated projection extends distally outwardly from the distal end of the plunger rod and is shaped to fit within the passageway of the elongated tip of the barrel. Structure for preventing proximal motion of the plunger rod with respect to the barrel after distal motion of the stopper to expel fluid through the passageway is provided. A needle assembly includes a cannula having a proximal end, a distal end and a lumen therethrough and a hub having an open proximal end with a tapered cavity therein including a side wall tapered distally inwardly at a taper of about 4% to 8%. The cavity has a diameter of less than about 3.85 mm at the open proximal end. The hub includes a distal end joined to the proximal end of the cannula so that the lumen is in fluid communication with the cavity. A needle shield is removably connected to the hub so that the distal end of the cannula is in the needle shield. A package encloses the syringe assembly and the needle assembly.

In other embodiments the side wall of the tip has a taper of about 6% and the side wall of the hub has a taper of about 6%.

Another embodiment of the present invention includes a needle assembly with a cannula having a proximal end, a distal end, and a lumen therethrough and a hub having an open proximal end with a tapered cavity therein. The tapered cavity has a side wall tapered distally inwardly at a taper of from 4% to 8%, preferably 6%, and a diameter of less than about 3.85 mm at its open proximal end. The hub includes a distal end joined to the proximal end of the cannula so that the lumen is in fluid communication with the cavity.

DETAILED DESCRIPTION

Figure 1:
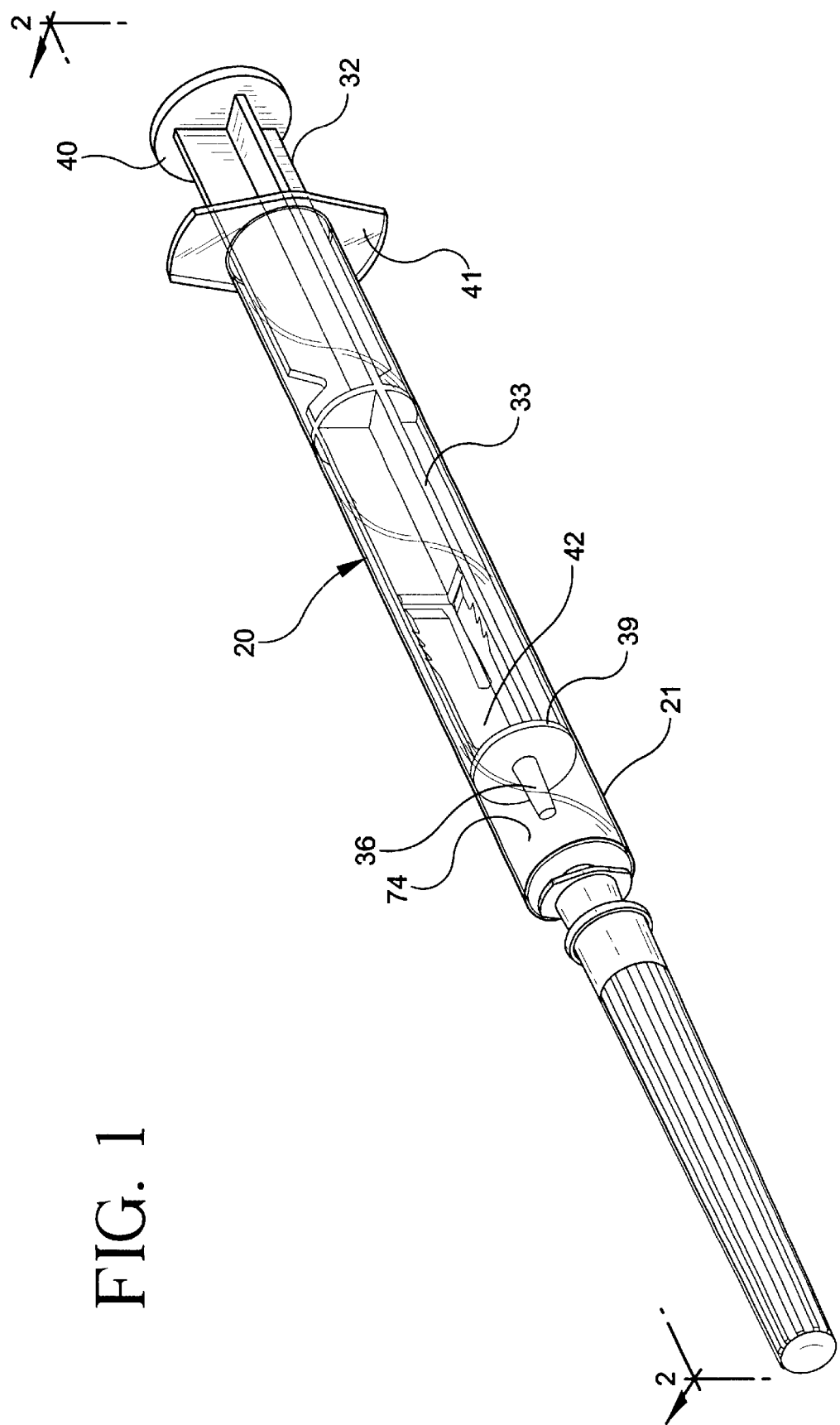
FIG. 1 is a perspective view of the single-use syringe assembly of the present invention with a needle assembly.
Figure 2:
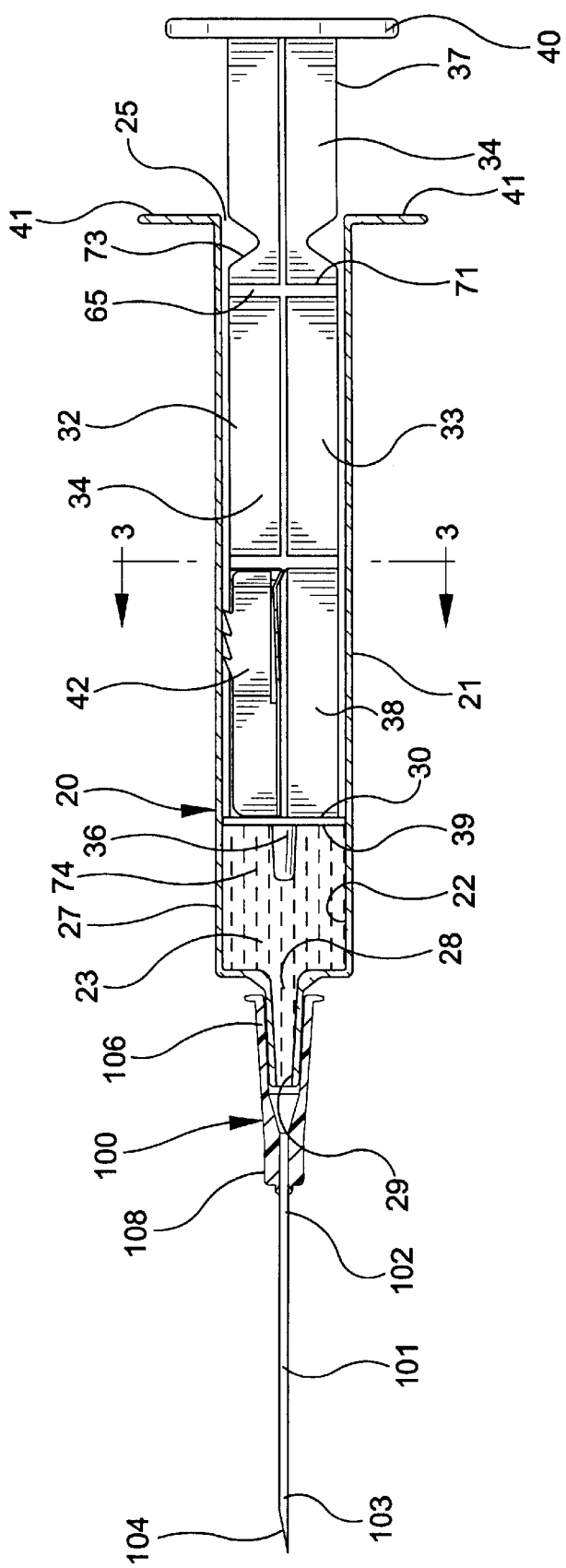
FIG. 2 is a partial cross-sectional view of the syringe assembly of FIG. 1 taken along line 2—2.
Figure 3:
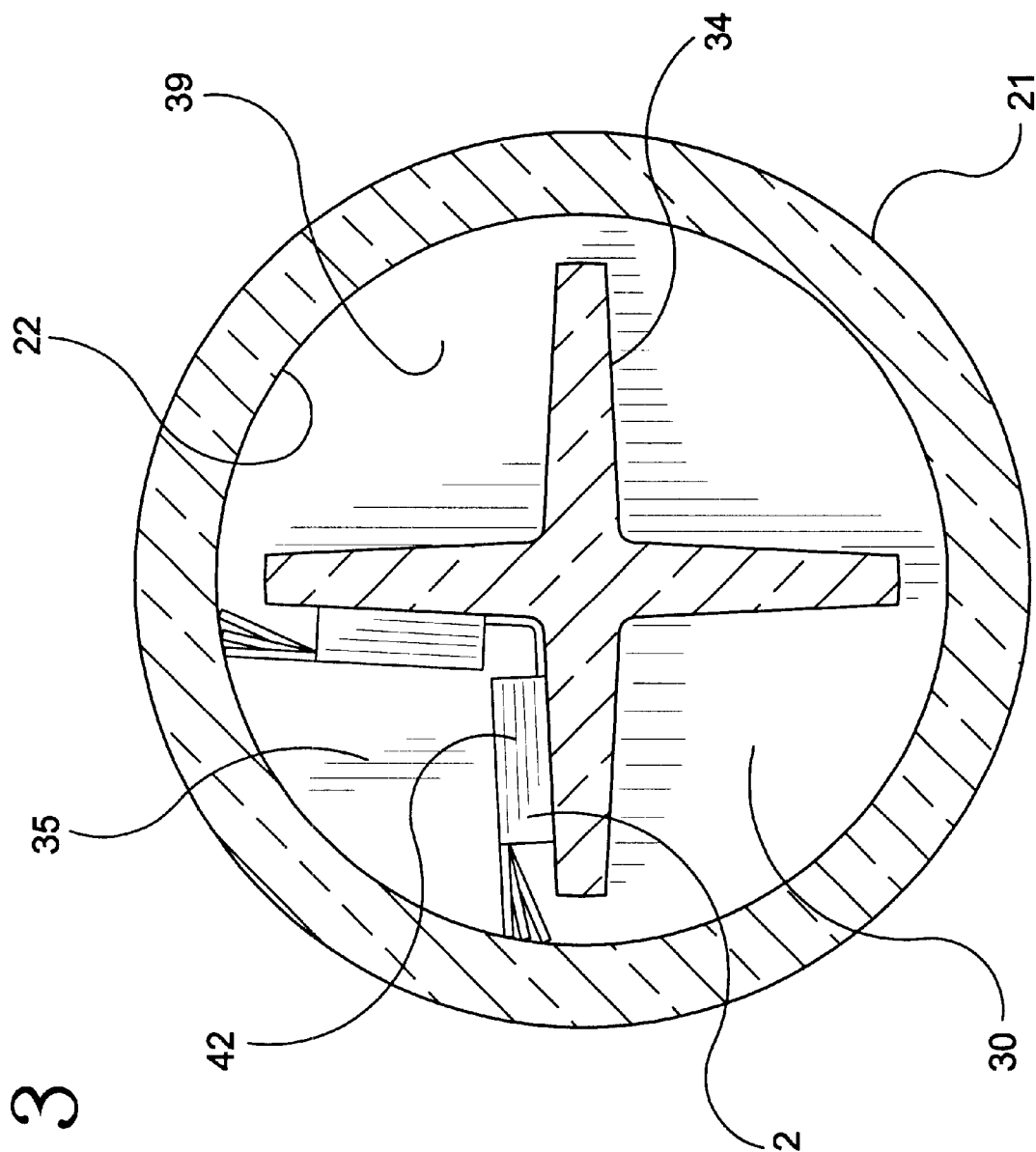
FIG. 3 is a cross-sectional view of the syringe assembly of FIG. 2 taken along line 3—3.
Figure 4:
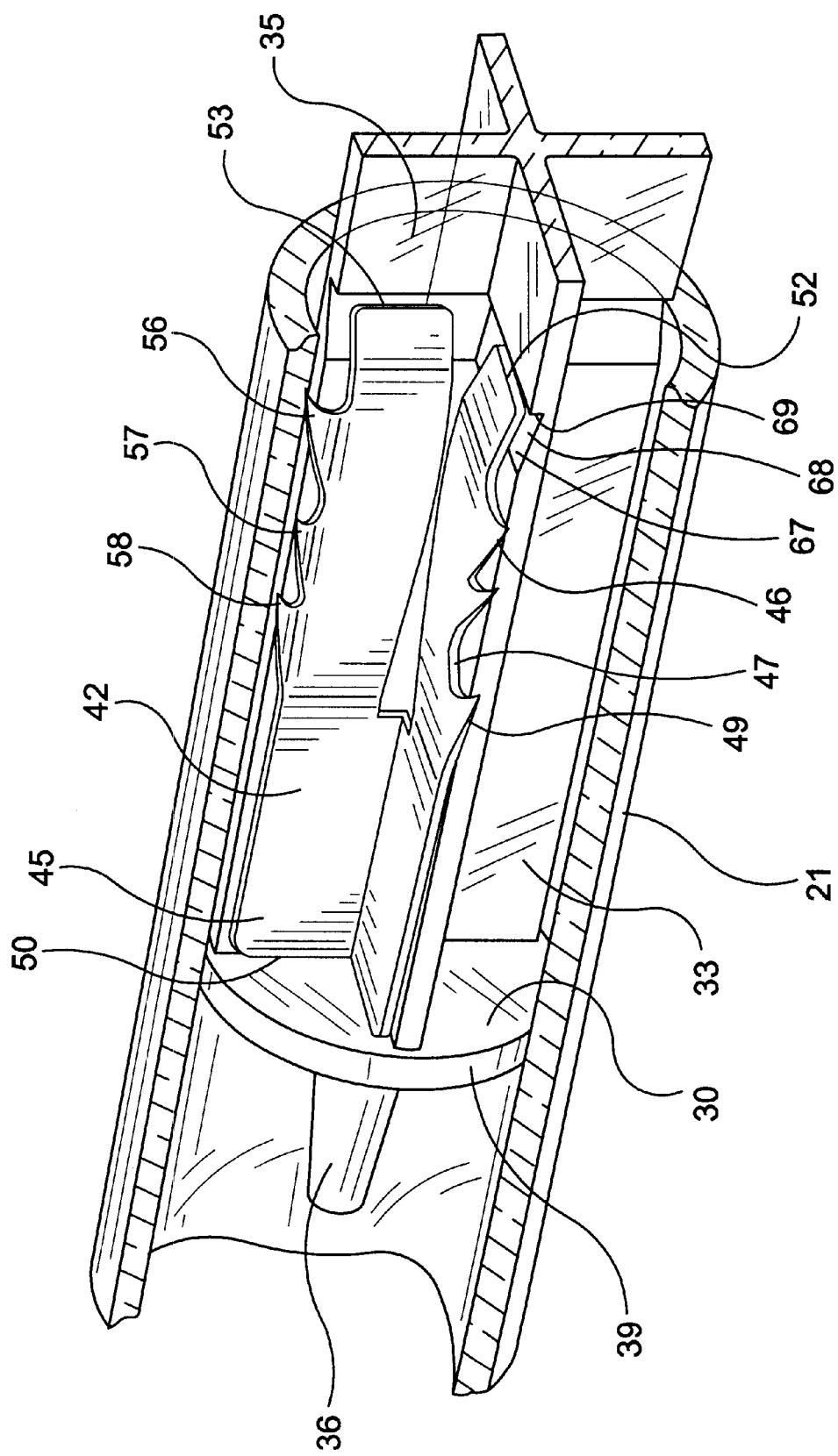
FIG. 4 is an enlarged partial cross-sectional perspective view of a portion of the syringe assembly of FIG. 1 containing the locking element.
Figure 5:
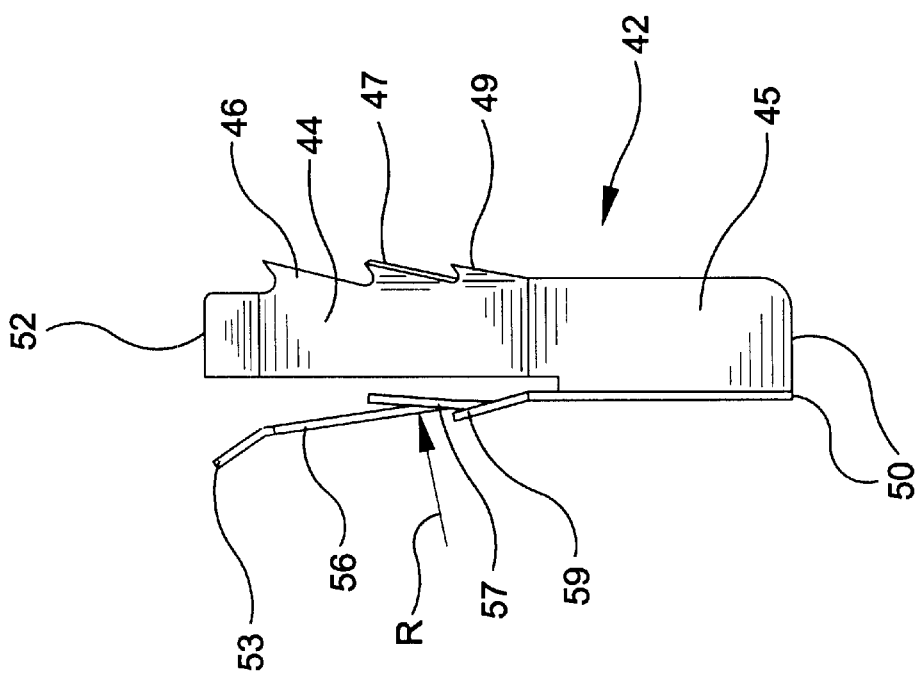
FIG. 5 is an enlarged top plan view of the locking element illustrating details of the locking element before forming.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

For the purposes of the description of the present invention, the term "distal end" is meant to refer to the end furthest from the person holding the syringe, whereas the term "proximal end" is meant to refer to the end closest to the holder of the syringe.

Adverting to FIGS. 1–16, a syringe assembly 20 having single use features, includes a barrel 21 having an inside surface 22 describing a chamber 23 for retaining fluid. Barrel 21 includes an open proximal end 25 and a distal barrel end 27. An elongated tip 29 extends distally outwardly from the distal end of the barrel and includes a passageway 28 therethrough in fluid communication with chamber 23. This tip has a diameter at its distal end of less than 3.8 mm, illustrated as dimension E in FIG. 15. The tip also has a side wall 31 tapered proximally outwardly at a taper of from 4% to 8%.

Syringe assembly 20 is preferably provided with a needle assembly 100 including a cannula 101 having a proximal end 102, a distal end 103 and a lumen 104 therethrough. A hub 105 includes an open proximal end 106 with a tapered cavity 107 therein and a distal end 108 joined to the proximal end of the cannula so that the lumen is in fluid communication with the cavity of the hub. Tapered cavity 107 includes side wall 109 tapered distally inwardly at a taper of from 4% to 8%. The cavity has a diameter of less than about 3.85 mm at its open proximal end, illustrated as dimension A in FIG. 14. When needle assembly 100 is connected to syringe barrel 21 elongated tip 29 of the barrel is positioned within cavity 107 of the hub.

The International Organization for Standards provides a standard for the Luer taper for syringes and needles which is adhered to by manufacturers of medical devices and fluid transfer devices throughout the world. This standard, ISO 594/1 is incorporated by reference into this specification. The standardization of luer fittings is a great benefit in healthcare and in laboratories by virtue of allowing connection of various fluid-handling components made by the same or different manufacturers. For example, several needles can be used with one syringe such as, a larger needle for filling the syringe and then a smaller needle for injecting. Syringes will mate with catheter fittings and stopcocks to provide fluid into a closed system. Also, almost all needle sizes can be combined with all syringe sizes for numerous uses thereby customizing the combination for the most efficacious or efficient use. However, with regard to the multiple use of hypodermic syringe devices, which are intended for single-use only, and which contributes to drug abuse and the transfer of contagious diseases, standardization of luer fittings is part of the problem. Almost any hypodermic needle whether found in garbage or misappropriated by a healthcare worker can fit almost any syringe creating a combination for the delivery of drugs and/or the transfer of disease. Herein lies a major advantage of the present invention. The needle assembly of the present invention has a hub cavity diameter at the proximal end of less than about 3.85 mm. The ISO standard provides for a tip diameter on the distal end of the syringe tip ranging from 3.925 mm to 4.027 mm for semi-rigid materials such as plastic, the most common syringe material. Accordingly, the needle assembly of the present invention will not fit on a larger standard ISO luer tip. Likewise, the distal end of the luer tip of the syringe of the present invention has a diameter E of less than 3.8 mm while the ISO standard diameter for an opening of the female conical luer fitting ranges from 4.270 mm to 4.315 mm so that a standard hypodermic needle will not properly engage the syringe of the present invention. However, the needle hub diameter is most important and controlling since the syringe of the present invention is a single-use syringe and cannot be re-used.

The ISO standard specifies 6% taper for luer conical fittings. In the preferred embodiment of the present invention the side wall of the syringe barrel tip has a taper of about 6% and the side wall of the hub cavity has a taper of about 6%. The total included angle, a in FIG. 14 and b in FIG. 15 for a 6% luer taper is approximately 3.43 degrees.

Figure 15:
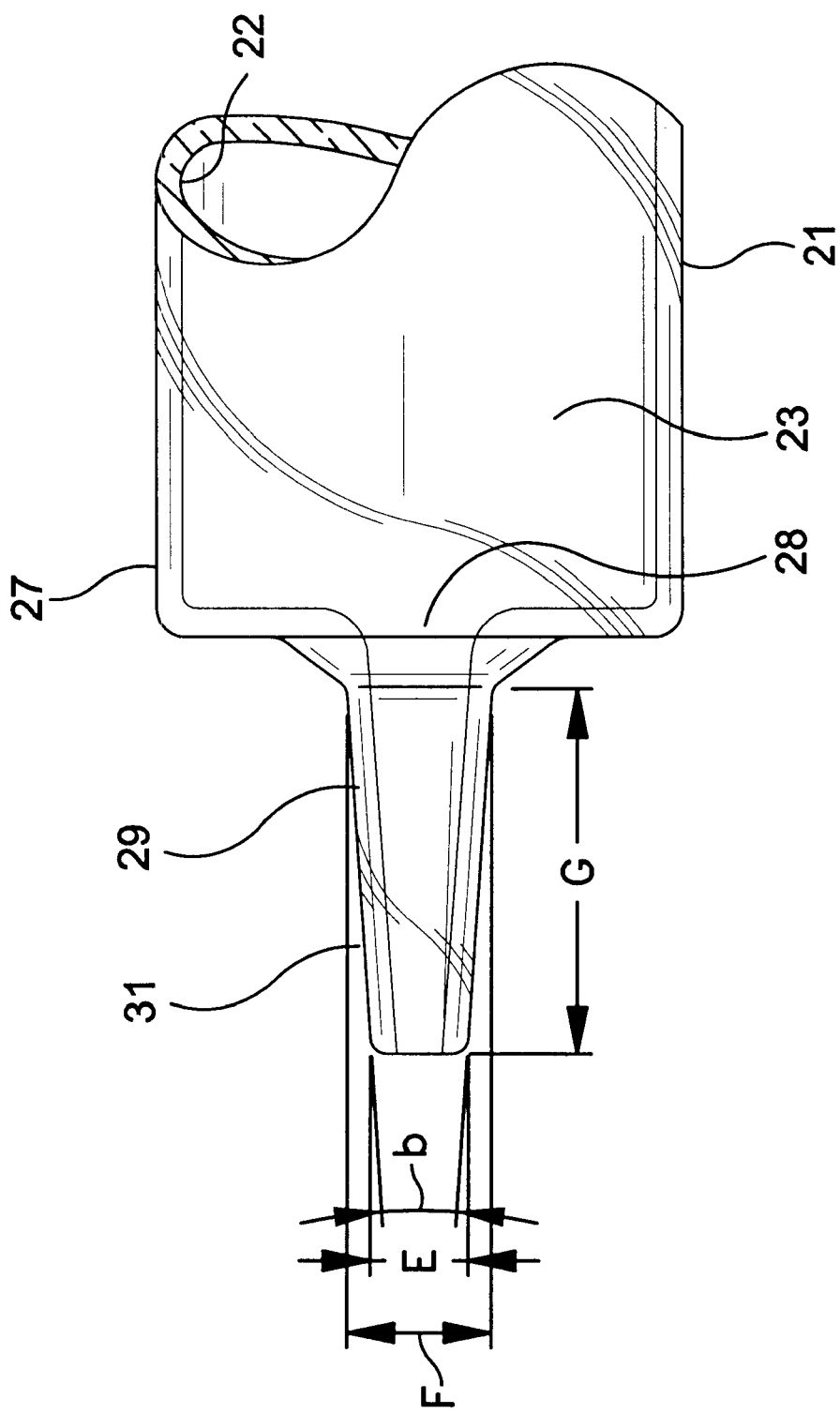
FIG. 15 is an enlarged side-elevational view of the distal end of the syringe barrel of the present invention.

Referring to FIG. 15, the ISO standard recites a tip diameter E of 3.925 mm to 4.027 mm and a minimum length G of 7.500 mm. The present invention desirably has a tip diameter E of less than 3.8 mm and preferably has a tip diameter of 3.4 mm and a tip length-of about 8.07 mm and a root diameter F of about 3.82 mm. In the preferred embodiment, the root diameter or largest diameter of the present syringe tip is smaller than the minimum diameter specified by ISO for a female conical fitting of 4.270 mm.

Figure 14:
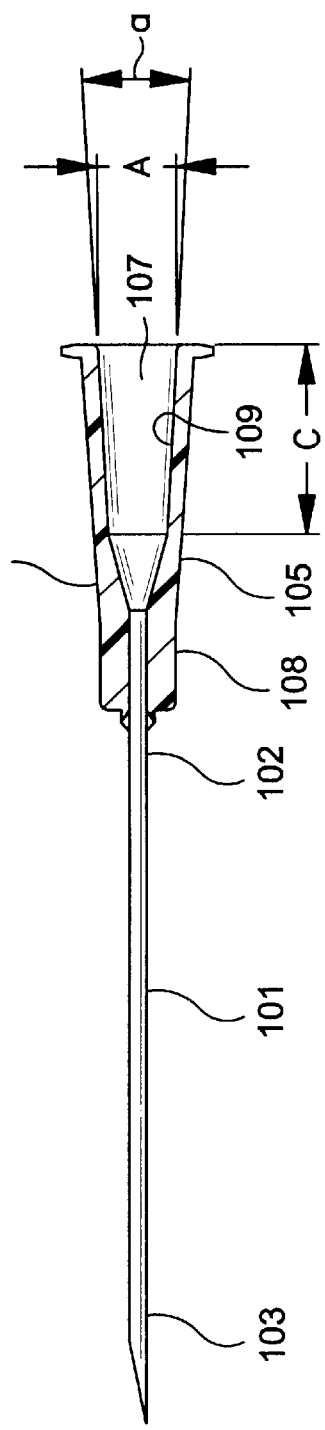
FIG. 14 is a cross-sectional view of the needle assembly of FIG. 13 taken along line 14—14.

Referring to FIG. 14, the ISO standard requires a diameter A at the open end of the female conical fitting from 4.270 mm to 4.315 mm while the present invention desirably has an opening diameter A of less than about 3.85 mm and preferably 3.73 mm so that even the smallest ISO specified luer tip (3.925 mm) will not fit the needle assembly of the present invention. ISO specifies a minimum depth for the conical female fitting of 7.500 mm and the preferred embodiment of the present invention has a depth of C 7.92 mm falling within the ISO standard. The reduced diameter hub cavity is an important feature of the present invention since it protects people from problems associated with multiple use by helping to prevent easy re-use of the needle assembly on another syringe.

The needle assembly of the present invention preferably, but not necessarily, includes an elongated needle shield 115 having an open proximal end 116, a distal end 117 and a side wall 118 therebetween defining a recess 119 in the shield. The shield removably engages hub 105 so that distal end 103 of the cannula is in the needle shield.

A plunger 32 includes a stopper 39 and a plunger rod 33 having an elongated body portion 34. The elongated body portion includes a longitudinal recess 35, a proximal end 37, and a distal end 38. In this preferred embodiment the longitudinal recess is v-shaped when viewed along the longitudinal axis of elongated body portion 34 with the narrowest portion of the recess being closest to the center or longitudinal axis of the elongated body portion. Stopper 39 is positioned at distal end 38 of the plunger rod and is preferably integrally formed with the plunger rod. The stopper is slidably positioned in fluid-tight engagement in the barrel while a portion of body portion 34 of the plunger rod extends outwardly from open proximal end 25 of the barrel. The plunger rod is accessible outside of open proximal end 25 of the barrel and is provided to move the stopper along the barrel to force fluid into and out of the chamber 23 through passageway 28. Disc-shaped plunger rod flange 40 is provided as a convenient structure for applying forces to move the plunger rod with respect to barrel 21. A flange 41 is also provided at the proximal end of the barrel to facilitate handling and positioning the syringe and for maintaining the relative position of the barrel with respect to the plunger rod during filling and medication administration.

It is within the purview of the present invention to include plunger rods and stoppers which are separately formed or integrally formed of the same material or different materials, such as in two-color molding, or separately formed of the same or different materials and joined together by mechanical means, adhesive, ultrasonic welding, heat sealing or other suitable means. It is understood that the plunger rod assembly of this preferred embodiment is merely illustrative of these many possibilities.

An elongated projection 36 extends distally outwardly from distal end 38 of plunger rod 33. Elongated projection 36 is shaped to fit within passageway 28 of elongated tip 29. This is an important feature of the present invention because the elongated projection moves additional volume of medication out of the syringe chamber which is preferably approximately equal to the volume of the elongated projection. This feature substantially eliminates wasted medication which would normally be left in the syringe barrel after the plunger rod is moved to its distal-most position within the syringe barrel. It is preferred that the distal end of the plunger rod and/or the stopper be configured to match the interior structure of the barrel and that the elongated projection be similarly shaped to the interior passageway of the syringe barrel tip so that there is little space between these components in order to maximize the amount of medication which is injected and minimize the amount of medication which remains in the syringe barrel after injection. In this preferred embodiment, stopper 39 is integrally molded with plunger rod 33 and elongated projection 36 resulting in a one-piece plunger 32. As indicated above, it is within the purview of the present invention to include a separate stopper. When a separate stopper is included the elongated projection may be integrally formed or attached to the stopper or, as will be explained in more detail hereinafter, the separate stopper may include an aperture through which the elongated projection extends. This important feature of the present invention not only results in substantial savings for mass inoculations or other programs involving many syringes but it also reduces the incentive for improper tampering of the syringe since little or no medication remains in the syringe after injection. This feature is particularly desirable if the medication is a narcotic or other addicting substance because residual amounts of medication after injection are not desirable.

A locking element 42 is positioned in the barrel and partially within longitudinal recess 35 between the plunger rod and the inside surface 22 of the barrel. Longitudinal recess 35 of the plunger rod acts as a pathway for longitudinal motion of the locking element relative to the elongated body portion of the plunger rod. Element 42 includes a proximal portion 44. Proximal portion 44 includes a proximally and outwardly facing locking barb 46. In addition proximal portion 44 also includes two additional anti-twist locking barbs 47 and 49 which are preferably not facing in the same direction as locking barb 46. Locking barbs 47 and 49 are optional but important in helping prevent misuse of the instant syringe to overcome the single use function by twisting the plunger rod as will be explained in more detail hereinafter.

Figure 6:
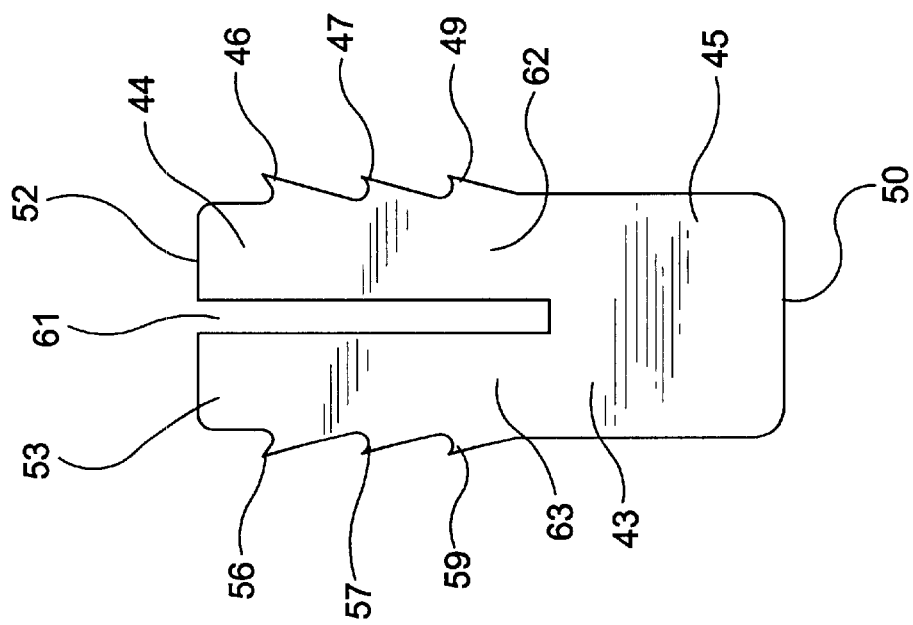
FIG. 6 is a side-elevational view of the locking element.
Figure 7:
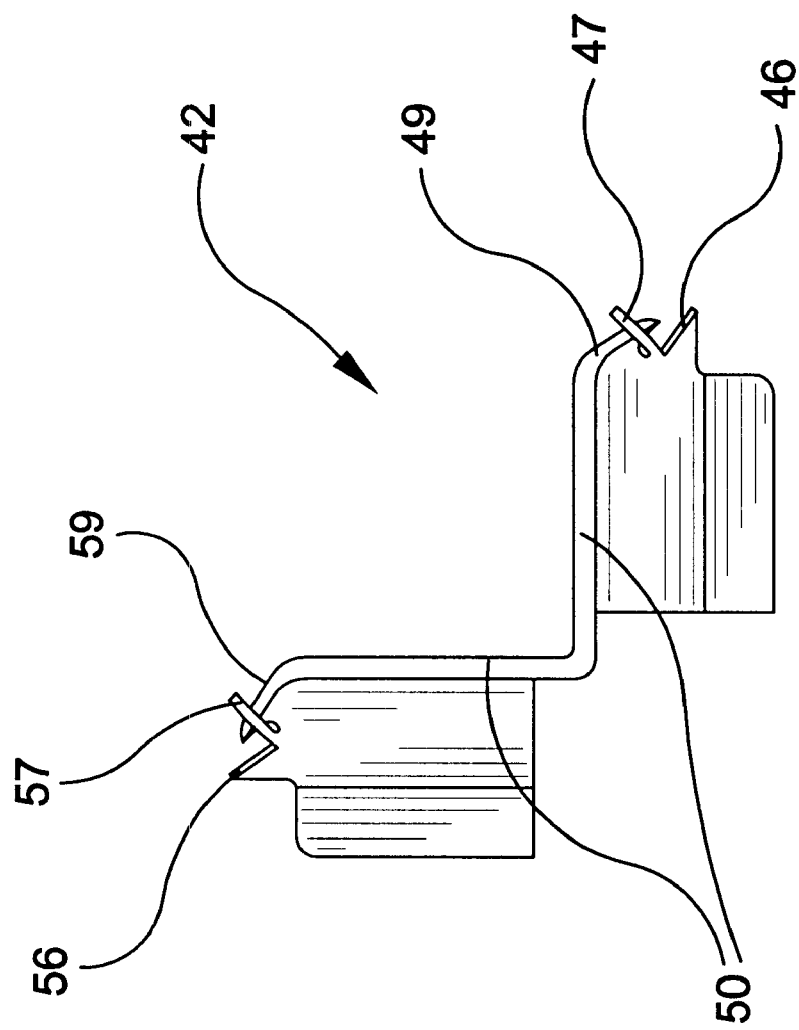
FIG. 7 is a side-elevational view of the end of the locking element of FIG. 6.
Figure 8:
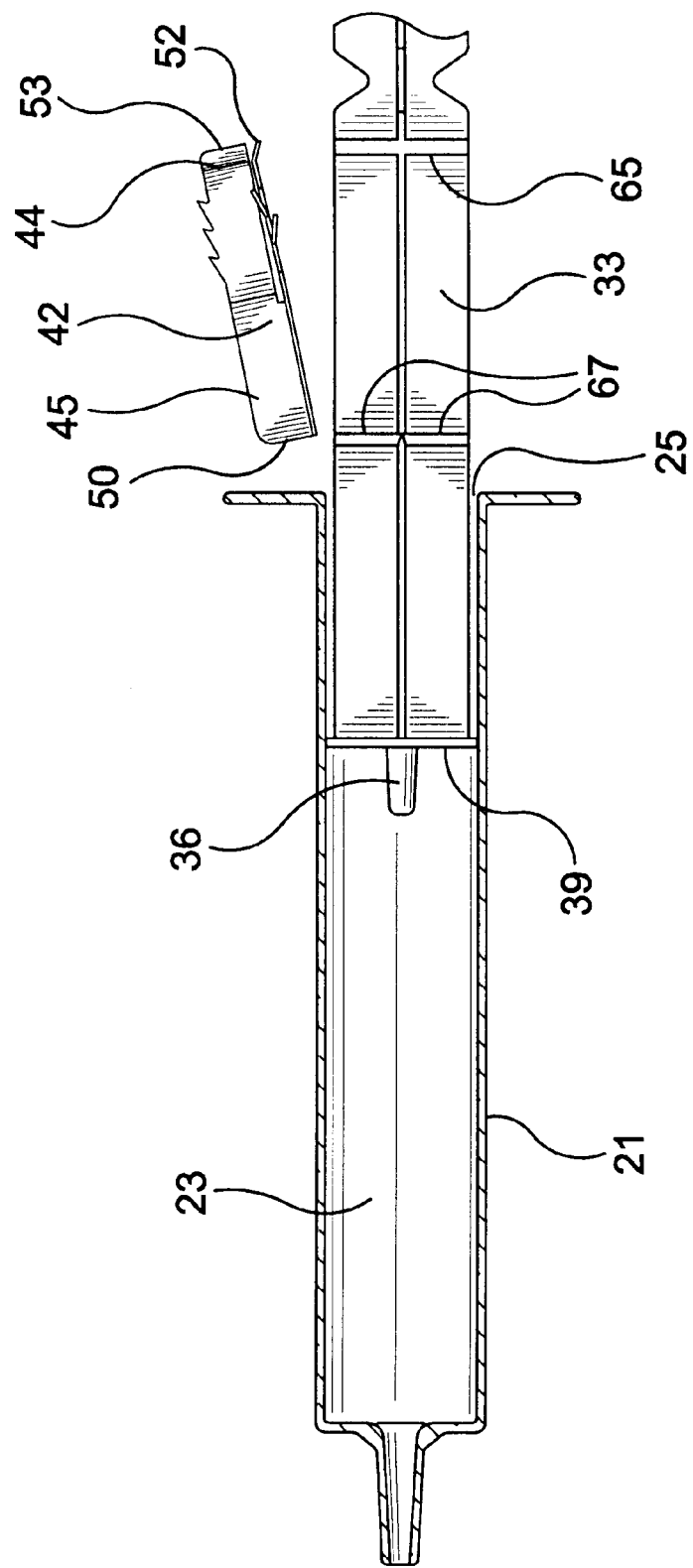
FIGS. 8–11 illustrate the assembly and use of the single-use syringe assembly.
Figure 9:
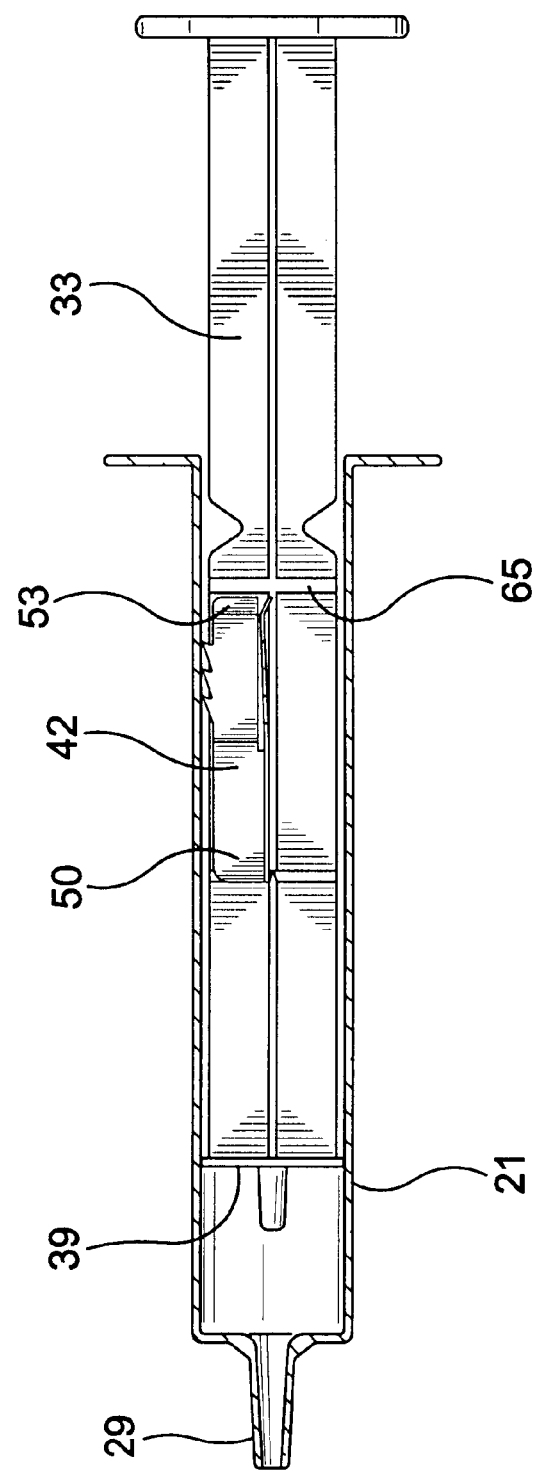

It is preferred that locking barb 46 remain in the plane of sheet metal 43 while anti-twist locking barbs 47 and 49 are positioned at angles with respect to the locking barb preferably with each anti-twist locking barb being angled away from the locking barb 46 on different sides of the locking barb as best illustrated in FIG. 6. Where anti-misuse features are desirable it is preferred that at least two proximally and outwardly facing non-parallel locking barbs are provided. If two barbs are used it is preferable that these barbs are included with respect to each other at an angle within the range of about five (5) degrees to ninety (90) degrees.

It is desirable that three barbs are provided with one of the three locking barbs remaining substantially parallel to the body structure or in the plane of the body material, and the other two barbs being bent at angles away from this barb. It is desired but not necessary, if sheet material construction is used for the locking element, that one of the locking barbs should be oriented in the plane of the sheet material. The second locking barb or first anti-twist locking barb is preferably located in a plane positioned at an angle of between about five (5) degrees to ninety (90) degrees with respect to the plane of locking barb and the third locking barb or second anti-twist locking barb is located in a plane positioned at an angle of between about five (5) degrees and ninety (90) degrees with respect to the plane of the locking barb and preferably oriented toward the opposite side of the plane of the locking barb as the first anti-twist locking barb. For the purposes of the present invention the non-parallel relationship of the barbs, when the locking element is made of sheet metal, is established by bending one or more of the barbs so that the barbs point in different directions as a result of the barb or barbs being bent.

Locking element 42 also includes a distally and inwardly facing resisting edge 50 and an inwardly facing driving edge 52 at proximal portion 44 of the locking element. For the purpose of describing locking element 42 the term "inwardly" shall mean toward a surface on the plunger rod body portion such as a surface along longitudinal groove 35, and the term "outwardly" shall mean facing generally toward inside surface 22 of barrel 21. Driving edge 52 is adapted to interact with longitudinal recess of the plunger rod to move the locking element along the barrel as the stopper is advanced along the barrel by force applied to the plunger rod. As will be explained in more detail hereinafter, driving edge 52 also, because of its orientation, allows proximal motion of the plunger rod with respect to the barrel during filling while helping to keep the locking element in a fixed position with respect to said barrel. Resisting edge 50 and the locking barbs are adapted to prevent proximal motion of plunger rod 33 with respect to barrel 21 after initial distal motion of the stopper on the plunger rod to expel fluid through passageway 28. Subsequent proximal motion of the plunger rod with respect to the barrel causes resisting edge 50 to engage elongated body portion 34 in the longitudinal recess 35 causing locking element 42 to move in a proximal direction wherein the locking barb 46 engages inside surface 22 of the barrel to prevent further movement and allowing only distal movement of the plunger rod with respect to the barrel.

In this preferred embodiment locking element 42 further includes a second inwardly facing driving edge 53 at proximal portion 44 and a second proximally and outwardly facing locking barb 56 adjacent to additional anti-twist locking barbs 57 and 59 which are angularly oriented away from second locking barb 56 and preferably non-parallel with respect to each other. Locking barbs 46, 47 and 49 and driving edge 52 are separated from second locking barbs 56, 57 and 59 and second driving edge 53 by longitudinal gap 61 so that driving edge 52 and second driving edge 53 extend proximally in cantilever spring-like fashion from distal portion 45 acting to force locking barb 46 and second locking barb 56 against the inside surface of the barrel. As will become more apparent hereinafter it is preferable to have a locking element with spring-like qualities such as a locking element formed of metal such as berelieum copper or stainless steel with stainless steel sheet metal being preferred for medical applications. It is preferred that the stainless steel sheet metal have a thickness of between about 0.003 inch (0.076 mm) to 0.20 inch (0.508 mm) when used in a syringe barrel having an inside diameter of about 0.333 inch (8.5 mm). Longitudinal gaps 61 divides proximal portion 44 into two cantilever spring arms 62 and 63 which are preferably bent along preferably variable radius R so that the distance across the locking element at the locking barbs is larger than the space available between the plunger rod and the inside surface of the syringe barrel. This configuration requires compression of the spring arms upon assembly and, as will be explained in more detail hereinafter, provides a slight pressure of the locking barbs against the inside surface of the barrel.

The syringe of the present invention may be used with a plurality of locking elements, for example, the preferred embodiment will accept up to four separate locking elements to provide additional mechanical resistance to multiple use. Also, a locking element and/or plunger rod may be shaped so that a single larger locking element engages areas further apart on the inside surface of the syringe barrel such as along 90 degrees to 360 degrees of the inside diameter of a circularly shaped syringe barrel.

An important feature of the instant invention is its ability to provide a syringe assembly having structure for limiting the volume of fluid with which can be taken into the chamber through passageway 28 and subsequently delivered. This feature assists in achieving substantially consistent delivery volumes from syringe to syringe and is useful in programs involving large numbers of subjects being injected with medication at the same time such as immunization programs. This feature also prevents misuse by limiting the volume the syringe assembly is capable of delivering. To limit delivery volume a barrier means such as delivery limiting barrier 65 is provided. Delivery limiting barrier 65 establishes the maximum proximal position of locking element 42 with respect to the elongated body portion of the plunger rod. The barrier function can be accomplished by various structures such as a raised rib positioned transversely along the surface of the plunger rod in the area of the longitudinal recess as will be described hereinafter. As the plunger rod is moved in a proximal direction along the barrel the locking element because of its spring action which forces the locking barbs against the inside surface of the barrel tends not to move with the plunger rod. The delivery limiting barrier provides an obstacle in longitudinal recess 35 over which locking element 42 cannot pass. Accordingly, when the locking element contacts delivery limiting barrier 65 it is forced along the barrel with the plunger rod. The delivery limiting barrier in this embodiment is a circular flange. It is within the purview of the instant invention to include barrier means which is fixed to the plunger rod such as delivery limiting barrier 65 or movable thereon to adjust the volume of the syringe. The instant invention also functions without barrier means wherein the volume chosen is visually determined through use of a graphic scale printed on the syringe barrel (not shown) or other means.

Another important feature of the instant invention which helps provide consistently uniform syringe assembly performance through large quantities of syringe assemblies is the inclusion of a ledge such as delivery ledge 67 running transversely across longitudinal recess 35. Delivery ledge 67 includes inclined surface 68 and vertical edge wall 69. Delivery ledge 67 is positioned at a distance which is approximately the overall length of the locking element from the proximal side of the stopper or any structure in the longitudinal recess defining the proximal most limit of the recess, such as wall 30. Delivery ledge 67 in the preferred embodiment is positioned at a distance of approximately the length of the locking element proximally from wall 30 so that edge wall 69 is positioned at a distance slightly longer than the length of the locking element from wall 30. Delivery ledge 67 is lower and less pronounced than the delivery limiting barrier because it is configured to allow the locking element to pass thereover when the locking element moves distally with respect to the plunger rod but to positively engage driving edges 52 and 53 with vertical edge wall 69 when the element moves proximally with respect to the plunger rod. In this preferred embodiment the delivery ledge is formed by a recessed-groove in recess 35, however, it is also within the purview of the instant invention to include a delivery ledge formed of a raised projection such as a raised rib.

Initially, the locking element will slide along the longitudinal recess of the plunger rod while air is being forced from the chamber through the passageway in the needle cannula until the locking element abuts against delivery limiting barrier 65. Then the locking element will move with the plunger rod toward the distal end of the syringe barrel. In use, when drawing medication into the chamber through the needle cannula, the plunger rod will move in a proximal direction while the locking element will tend to remain stationary with respect to the barrel until it abuts against support wall 30. This position, as will be explained in more detail hereinafter, defines the maximum volume of the syringe. At this point, medication may be delivered from the syringe by moving the plunger rod in a distal direction with respect to the barrel such as by applying force to disc-shaped plunger rod flange 40. As the plunger rod moves toward the distal end of the barrel driving edges 52 and 53 tend to engage the plunger rod surface in the longitudinal recess and travel with the plunger rod. In almost all cases this phenomenon will occur readily because of the higher hardness of the locking element which is forced by its spring action against the plunger rod longitudinal recess. However, to assure that reliable and consistent operation from syringe assembly to syringe assembly delivery ledge 67 through its vertical ledge 69 further facilitates the engagement of driving edges 52 and 53 and the plunger rod longitudinal recess 35. It is desirable to shape the delivery ledge so that portions of the locking element pass readily over it when the locking element moves distally with respect to the plunger rod but to engage the driving edges 52 and 53 when the motion is reversed. To this end delivery ledge 67 is shaped to have inclined surface 68 at is distal side and vertical edge wall 69 at its proximal side. It is also within the purview of this invention to include a delivery ledge which is raised from the surface of the plunger rod longitudinal recess 35 to accomplish the same result.

A tamper resistant barrier 71 is positioned transversely with respect to the plunger rod wall to block access to the locking element through open end 25 of the barrel in order to prevent unwanted tampering with the locking element to defeat the single use function of the instant invention. It may be possible to use a long instrument such as forceps to reach in and disengage the locking element or to forcibly remove it. Tamper resistant barrier 71 acts to prevent this access. In the preferred embodiment, although it is not necessary, the tamper resistant barrier 71 and delivery limiting barrier 65 occupy the same position along the axial length of the plunger rod. A different embodiment of the plunger rod wherein the delivery limiting barrier and the tamper resistant barrier are at separate positions along the plunger rod will be described hereinafter.

Another feature of the instant invention which helps prevent misuse is the inclusion of a weakening means located between tamper resistant barrier 71 and the proximal end of the plunger rod. In this embodiment the weakening means includes an area of reduced transverse cross-sectional thickness 73, which helps to allow the plunger rod to break if excessive and unnecessary amounts of force are applied at the proximal end. A person attempting to defeat the single use function of the instant invention may attempt to do so by twisting or bending the plunger rod in order to distort or defeat the locking element. To avoid this possibility the area of reduced transverse cross-sectional thickness in the plunger rod will greatly reduce the resistance of the plunger rod to bending or torsional forces causing it to fail.

To further resist torsional force supplied to the proximal end of the plunger rod and in order to promote failure of the plunger rod at the area of reduced transverse cross-sectional, thickness anti-twist locking barbs 47 and 49 and additional anti-twist locking barbs 57 and 59 which are angled out of the plane of locking barbs 46 and 56 respectively are oriented to dig into the syringe barrel wall upon the application of torsional force. For example, anti-twist locking barbs 47 and 57 would tend to resist torsional rotation in one direction while anti-twist locking barbs 49 and 59 would tend to resist torsional rotation of the plunger rod with respect to the barrel in the opposite direction.

Figure 10:
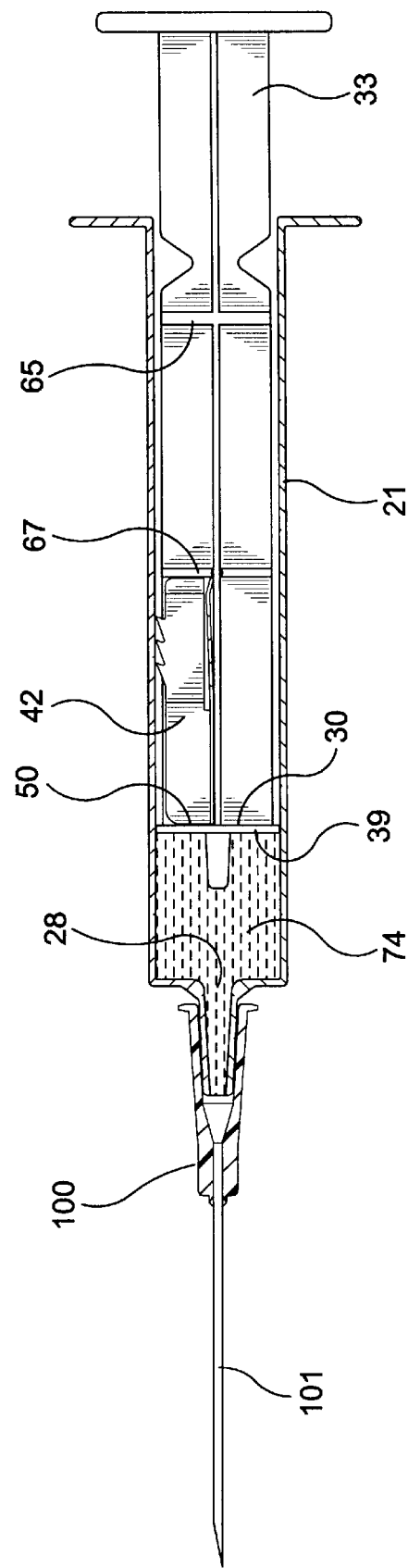
Figure 11:
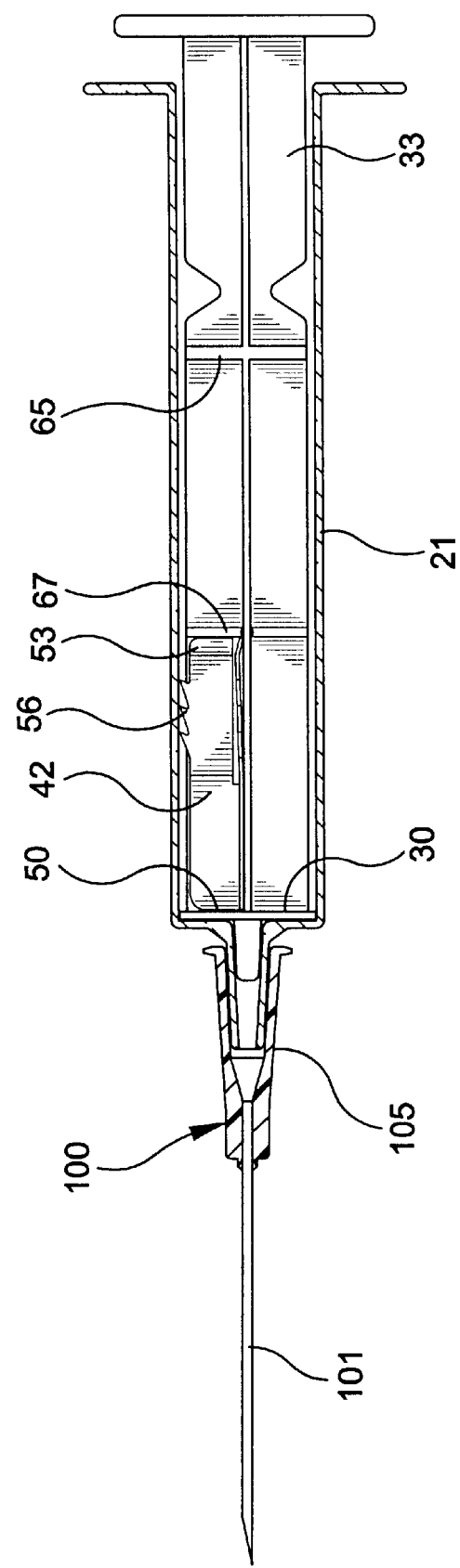
Figure 12:
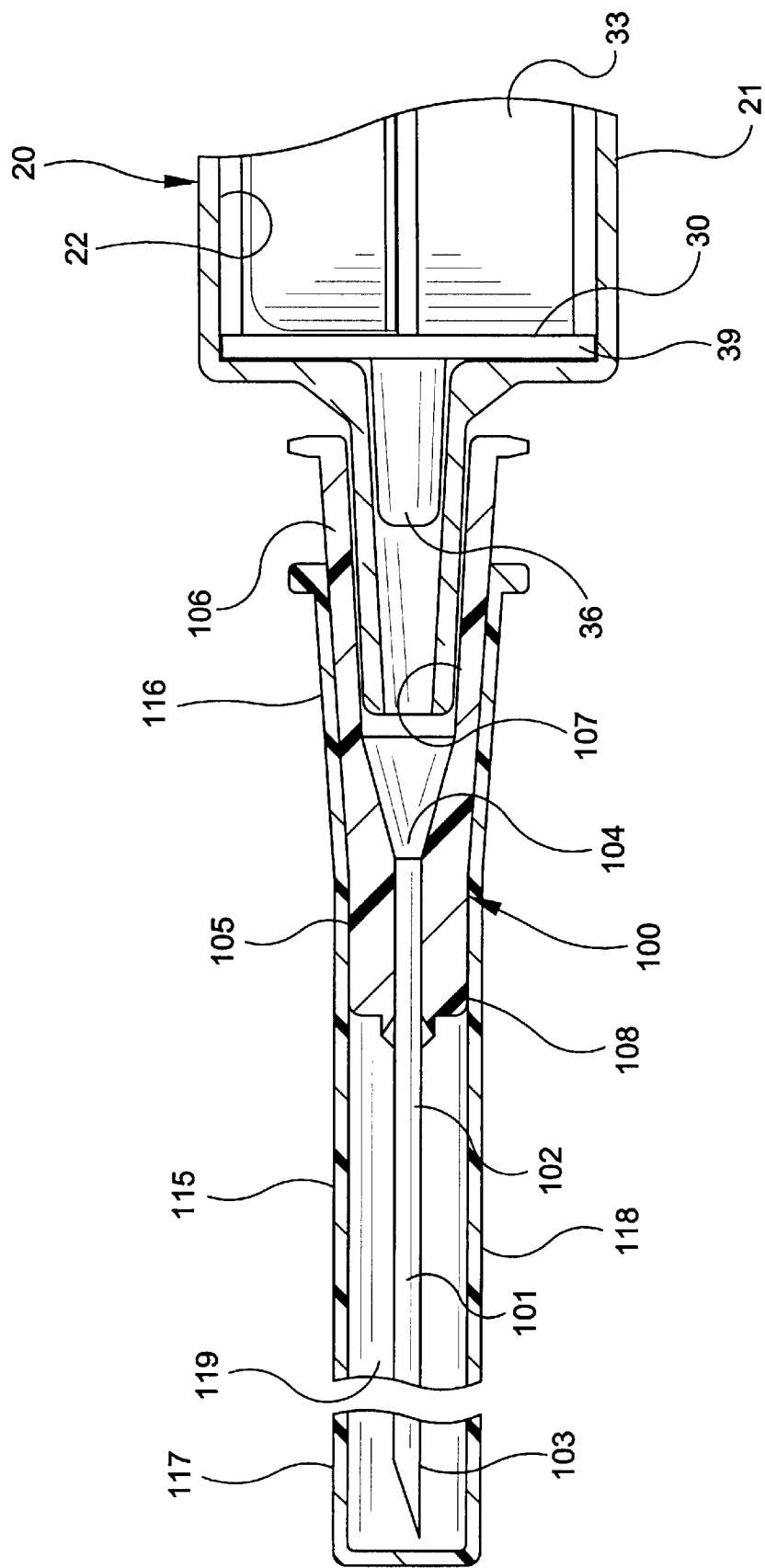
FIG. 12 is an enlarged partial cross-sectional view of the single-use syringe assembly of FIG. 11 with a needle shield attached.
Figure 13:
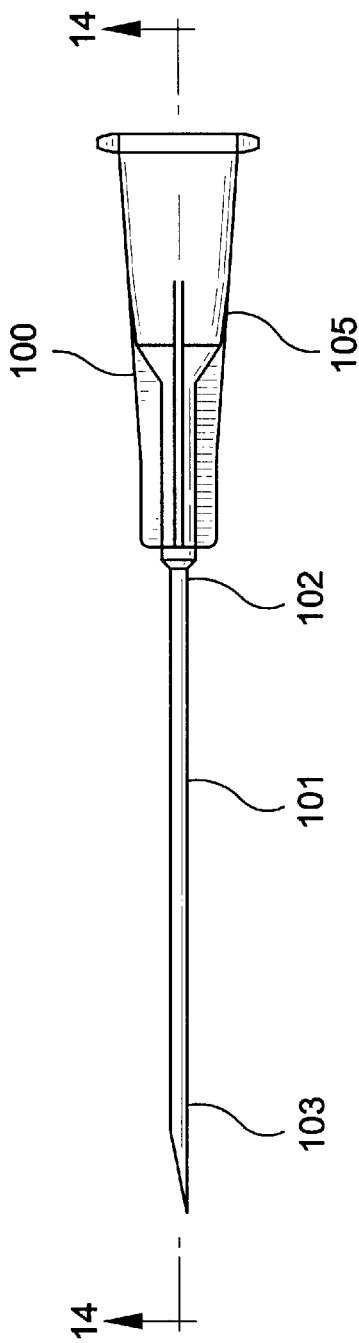
FIG. 13 is a side-elevational view of the needle assembly of the present invention.

Referring now to FIGS. 8–11 the syringe assembly of the instant invention may be assembled by placing the stopper in the barrel with the plunger rod projecting outwardly from open end 25 of the barrel and then placing locking element 42 in the longitudinal recess in a position which is distal to delivery limiting barrier 65 and then forcing the stopper and plunger rod along the barrel until the stopper is in about its distal-most position. During motion of plunger rod 33 locking element 42 will, because of its spring action and locking barbs, remain substantially in one position with respect to the barrel until driving edges 52 and 53 contact delivery limiting barrier 65 and causes the locking element to move with the plunger rod to the position illustrated in FIG. 9. At this time the cannula, if it is not already in fluid communication with a source of medication, may be placed in a stoppered vial containing medication to be injected (not shown) and the plunger rod withdrawn so that medication 74 is drawn into the chamber as best illustrated in FIG. 10. During the step of drawing medication into the chamber the locking element 42 remains in a fixed position with respect to the barrel. This position of the locking element relative to the barrel defines the maximum volume which the syringe assembly will deliver and is established when support wall 30 of the plunger rod contacts resisting edge 50 of the locking element. Further proximal motion of the plunger rod will not occur because the locking element barbs will engage barrel inside surface 22 to resist this motion. The syringe is now ready for administering medication to a patient using known safe procedures. After the medication 74 is expelled from the syringe through passageway 28 and cannula 101 the syringe assembly of the instant invention will be in the position illustrated in FIG. 11. While medication is being delivered the locking element will move with the plunger rod along the barrel in a proximal direction because driving edges 52 and 53 are engaging the plunger rod with enough force to prevent any slipping. To facilitate the motion of locking element 42 toward the distal end of the barrel delivery ledge 67 is provided on the preferred embodiment to help improve the engagement between driving edges 52 and 53 and the plunger rod.

After delivery of the medication stopper 39 and plunger rod 33 are at about their distal-most position with respect to barrel 21. Withdrawal of the plunger rod from the barrel may not take place because at this position the proximally and outwardly facing locking barbs are engaging the barrel preventing proximal motion of the locking element with respect to the barrel while the locking element is resisting proximal motion of the plunger rod with respect to the barrel through, in this preferred embodiment, contact between resisting edge 50 of the locking element and support wall 30 of the plunger rod. The syringe of the instant invention has been used once and cannot be used again and can be properly discarded. Any attempt to dislodge the locking element by applying torsional force to the plunger would will be resisted by the locking element and possibly cause the plunger rod to fracture or break at the area of reduced transverse cross-sectional thickness 73. Also, an attempt to subsequently remove or disarm the locking element will be resisted by tamper resistant barrier 71.

Figure 16:
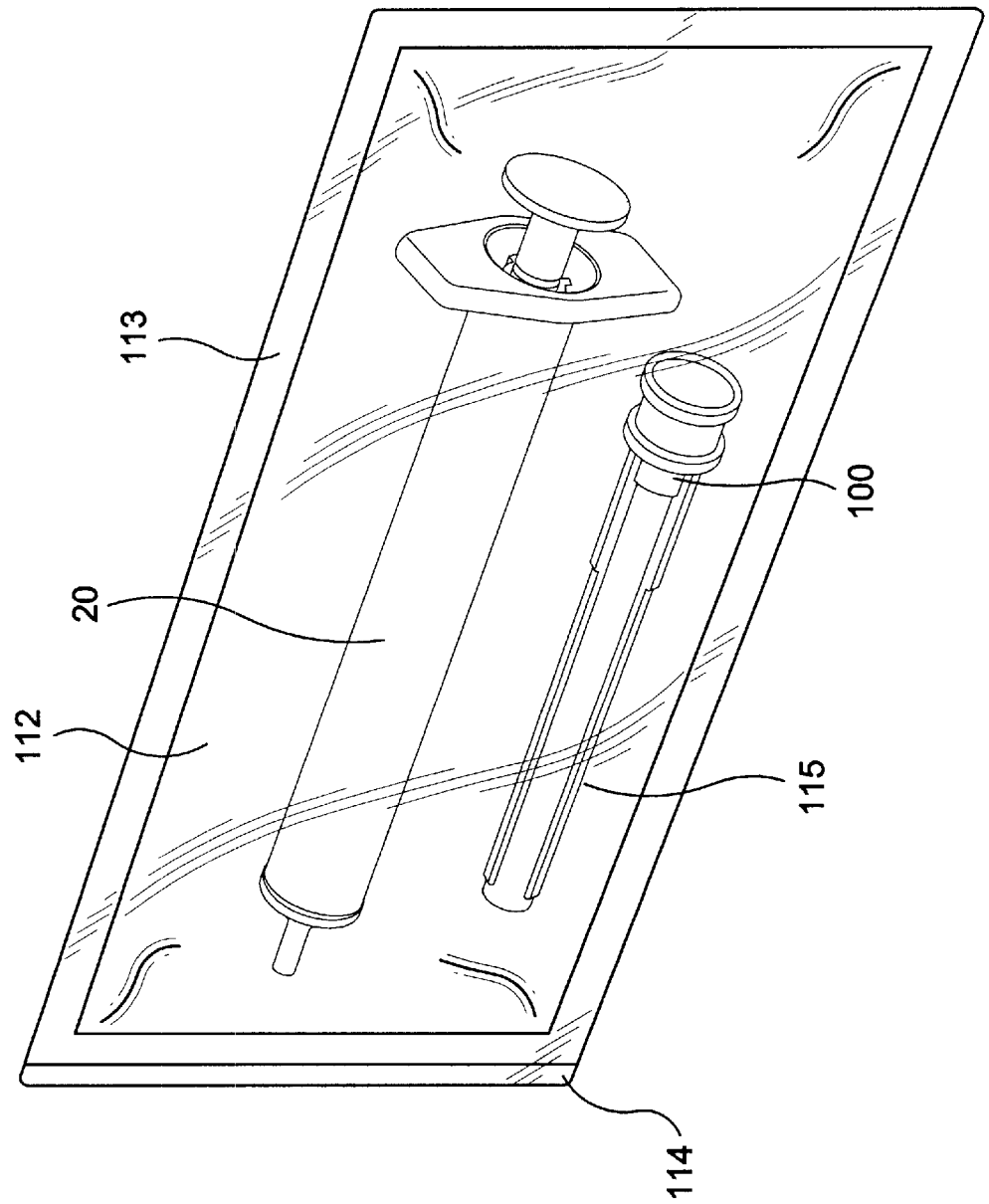
FIG. 16 is a perspective view of the preferred embodiment of the present invention including a syringe assembly and needle assembly in a sealed package.

Referring to FIG. 16, syringe assembly 20 and needle assembly 100 with needle shield 115 are preferably, before use, placed in a package 112 which functions as a microbial barrier and sterilizing the contents along with the package using a method such as radiation sterilization, autoclaving or the like. Package 112, in this embodiment, is sealed around its periphery 113 having an unsealed portion 114 along one side to allow the user to easily peel the package sides apart to gain access to the syringe and needle assembly. The syringe assembly may be packaged with the needle assembly attached or not attached. It is preferred to package the needle assembly unattached to the syringe assembly in a position aligned with and positoned adjacent to the syringe assembly in the package. This arrangement, as illustrated in FIG. 16, provides a most economical package, because the package length is essentially reduced by the length of the needle assembly.

Providing the needle assembly and shield with the syringe assembly in one package is an important feature of the present invention. As mentioned hereinabove, the syringe assembly of the present invention is a single-use syringe which will not function after the complete dose is delivered. Having such a syringe with a conventional ISO standard barrel tip and needle assembly hub would allow removal of the needle assembly after the injection. The needle assembly could then be used with a wide variety of other functional syringes where it could potentially transfer a disease or facilitate illegal drug usage. By providing the reduced diameter cavity in the hub of the present invention, the needle assembly, if improperly removed would not be able to be used with other syringes. The walls of the syringe can be molded or contoured so that any attempt to open up the tapered cavity of the hub would cause the hub to fall apart due to the absence of enough material in the hub to allow sizing it to the ISO standard size. This can be accomplished by having a ring or recess around the periphery of the hub defining an area of thin cross-section. Further, there is no incentive to reuse a used needle assembly of the present invention since every syringe assembly will come with its own sterile unused needle. Accordingly, the present invention can be a major contributor in helping to prevent syringe and needle assembly re-use.

Figure 17:
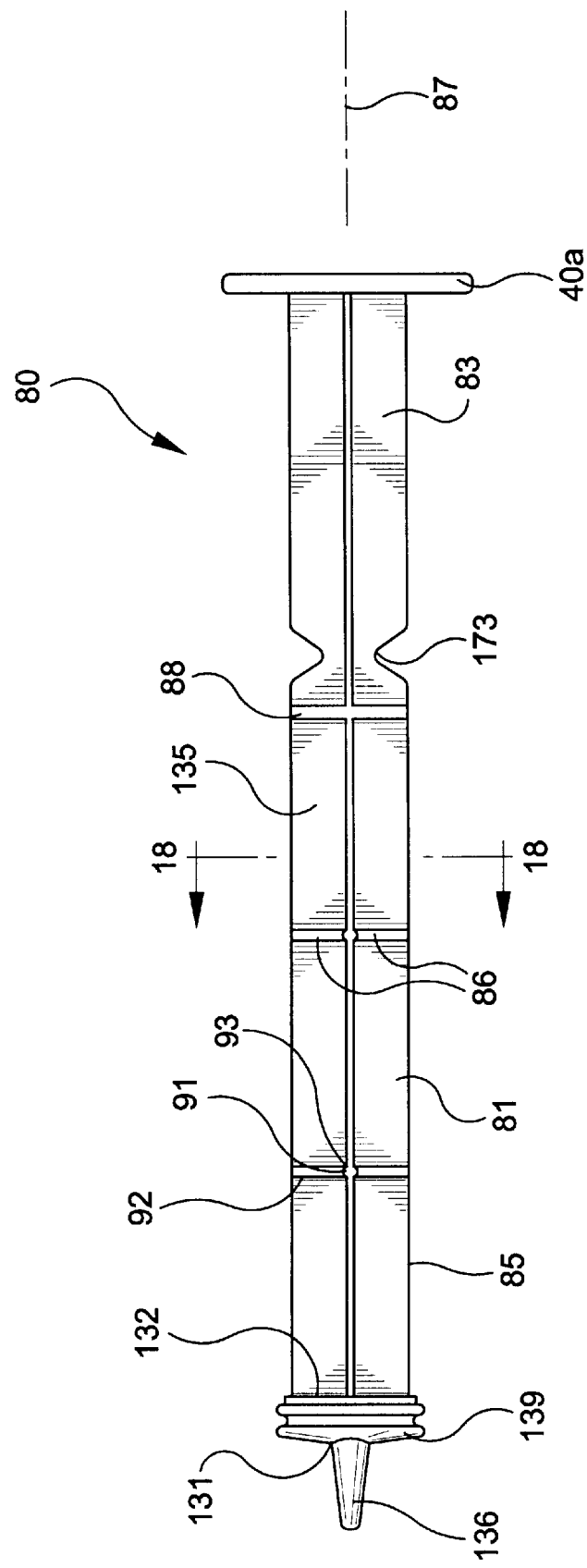
FIG. 17 is a side-elevational view of an alternative plunger rod assembly for use in the present invention.
Figure 18:
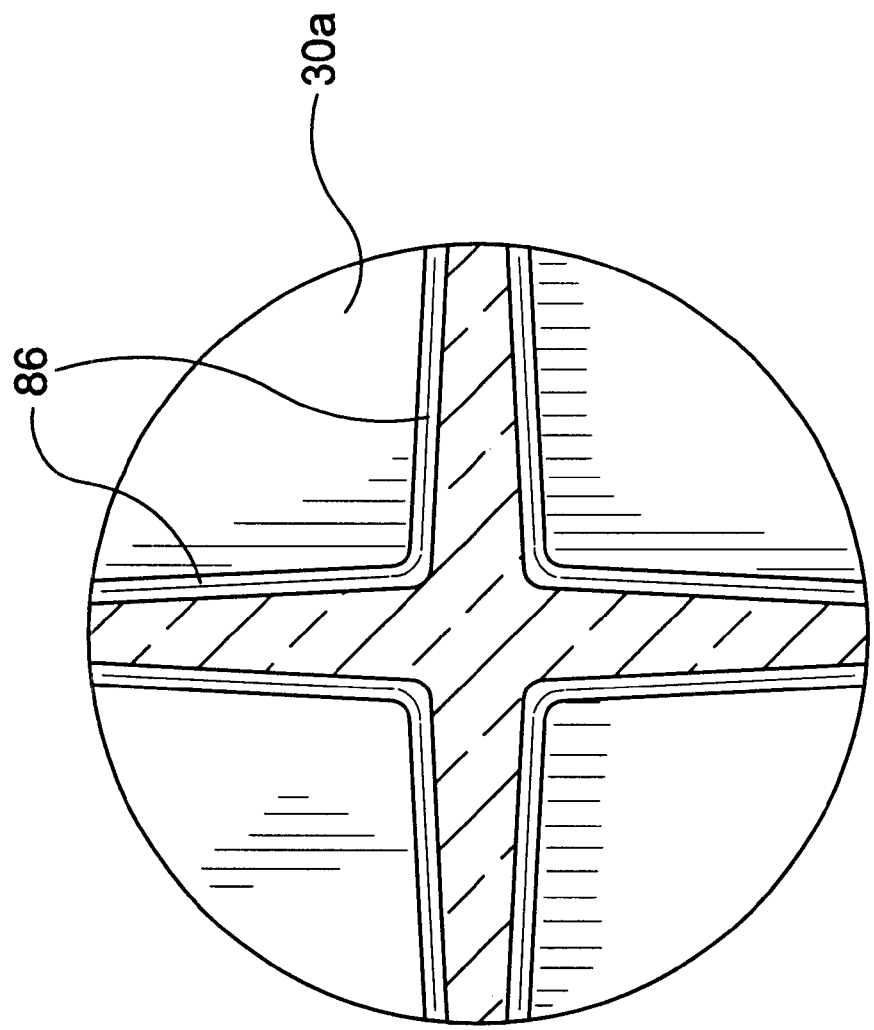
FIG. 18 is a cross-sectional view of the plunger rod assembly of FIG. 17 taken along line 18—18.

Adverting now to FIGS. 17 and 18, an alternative embodiment of the plunger rod and stopper of the instant invention is illustrated. In this embodiment the barrel and locking element although not shown are identical to the embodiment of FIGS. 1–16. In this embodiment an alternative plunger rod and stopper assembly 80 includes a plunger rod 81 having a proximal end 83 and a distal end 85. A stopper 139 at distal end 85 is slidably positioned in fluid-tight engagement in the barrel (not shown). Plunger rod 81 includes an elongated projection 136 extending distally outwardly from the distal end of the plunger rod. The elongated projection is shaped to fit within the passageway of the elongated tip of the syringe barrel (not shown). In this embodiment, stopper 139 is a separate element made of elastomeric material. Elongated projection 136 projects through aperture 131 and stopper 139 and is formed integrally with plunger rod 81. The elongated projection could also be integrally formed of the elastomeric material of the separate stopper.

Plunger rod 81 includes barrier means on the body portion for limiting the delivery volume of the syringe assembly by establishing the maximum proximal position of the locking element (not shown) with respect to elongated body portion 82 of the plunger rod. In this embodiment barrier means includes raised rib 86 running transversely across longitudinal recess 135 of elongated body portion 82. The plunger rod also includes stopper support means including wall 132 adjacent to stopper 139 for supporting the stopper during distal motion of the stopper with respect to the barrel. Wall 132, in this embodiment, is a support flange positioned transversely with respect to longitudinal axis 87 of elongated body portion 82. The plunger rod also includes tamper resistant barrier 88 in the shape of a barrier flange positioned transversely with respect to longitudinal axis 87. An area of reduced transverse cross-sectional thickness 173 is also provided in a position which is proximal to tamper resistant barrier 88 for allowing twisting failure of the plunger rod on application of excessive force to proximal end 83 of the plunger rod. Plunger rod 81 also includes delivery ledge 91 in the form of a raised projection running transversely along longitudinal recess 35a. Delivery ledge 91 includes inclined surface 92 and vertical edge wall 93. Delivery ledge 91 in this embodiment is positioned so that the distance between support wall 132 and vertical edge wall 93 is slightly larger than the length of the locking element (not shown). As with the embodiment of FIGS. 1–16, the positioning of the delivery ledge is determined by the distance between the support wall and the vertical edge wall.

The syringe barrel of the present invention may be constructed of a wide variety of rigid materials with thermoplastic materials such as polypropylene and polyethylene being preferred. Similarly thermoplastic materials such as polypropylene, polyethylene and polystyrene are preferred for the plunger rod. A wide variety of materials such as natural rubber, synthetic rubber and thermoplastic elastomers are suitable for the stopper. The choice of stopper material will depend on compatibility with the medication being used. In this embodiment the stopper, made of medical grade rubber, includes a partially hollow interior with an undercut ledge which is snap fit over a complementary structure on the plunger rod to secure the stopper to the plunger rod. A stopper and plunger rod may also be integrally formed of the same material or of different materials.

As previously recited, it is preferable that the locking element being fabricated from a material which is harder than the barrel and plunger rod material so that the locking barbs and resisting edge and driving edge may effectively engage these components. Resilient spring-like properties are also desirable along with low cost dimensionally consistent fabrication. With this in mind, sheet metal is the preferred material for the locking element with stainless steel being preferred for medical applications. Although the locking element of the preferred embodiment is fabricated from a single sheet, it is within the purview of the instant invention to include locking elements made of other forms of material such as wire and locking elements containing multiple parts and apparatus such as hinges and springs to achieve the function of the preferred locking element.

The syringe assembly of the present invention is a combination of features which together provides numerous advantages over the prior art in one product. Specifically, the syringe assembly is an effective single-use syringe which cannot be used after the full dose contained therein is delivered. This is an important feature to prevent re-use of used syringes for illegal drug usage or for uses which eventually transfer contagious diseases. In addition, the syringe assembly of the present invention provides a barrel and a distal end of the plunger that are contoured to maximize the removal of all fluid contained therein during the injection process. This is an especially desirable feature in mass immunizations due to the substantial amount of saved medication that would otherwise be wasted or lost in the syringe. With respect to other drugs such as narcotics, the almost complete delivery of the medication contained in the present syringe discourages tampering by those who want the drugs contained therein, since there is little or nothing to be salvages from a used syringe. Finally, the reduced diameter needle hub and barrel tip discourage further use because neither can be used with standard ISO fittings. In particular, the needle assembly can only be joined with the syringe of the present invention so there is no incentive to misappropriate the needle for further use. The needle hub can also be configured to break if there is an attempt to bore out the cavity to the larger ISO standard size. Finally, in the preferred embodiment of the present invention where the syringe assembly and needle assembly are provided in a package together, and there is no incentive to re-use the needle assembly of the present invention since every new syringe comes with a new needle assembly.

All of the above-mentioned features together provide a product that is ideally suited for mass immunization programs throughout the world. It provides a low cost, efficient, single-use syringe and features that prevent and discourage improper re-use. Clearly, the syringe assembly and needle assembly of the present invention is a distinct improvement over the prior art.

What is claimed is:

1. An operable syringe assembly comprising:
a barrel having an inside surface describing a chamber for retaining fluid, an open proximal end, a distal end, and an elongated tip extending from said distal end having a passageway therethrough in fluid communication with said chamber, said tip having a diameter at its distal end of less than 3.8 mm and a side wall tapered proximally outwardly at a taper of from 4% to 8%;
a plunger rod including an elongated body portion having a proximal end, a distal end, and a stopper at said distal end, said stopper being slidably positioned in fluid-tight engagement in said barrel, an elongated projection extending distally outwardly from said distal end of said plunger rod, said elongated projection being shaped to fit within said passageway of said elongated tip, said body portion extending outwardly from said open proximal end of said barrel; and
a locking element positioned in said barrel between said elongate body portion of said plunger rod and said inside surface of said barrel, said element having a proximal portion and a distal portion, said locking element including a proximally and outwardly facing locking barb, a distally and inwardly facing resisting edge and an inwardly facing driving edge at said proximal portion of said element, said driving edge adapted to interact with said body portion of said plunger rod to move said locking element along said barrel as said stopper is advanced along said barrel, said resisting edge and said barb adapted to prevent proximal motion of said plunger rod with respect to said barrel after initial distal motion of said stopper to expel fluid through said passageway wherein subsequent proximal motion of said plunger rod with respect to said barrel causes said resisting edge to engage said plunger rod causing said locking element to move in a proximal direction wherein said locking barb engages said inside surface of said barrel to prevent further movement and allowing only distal movement of said plunger rod with respect to said barrel.

2. The syringe assembly of claim 1 further including a needle assembly including a cannula having a proximal end, a distal end and a lumen therethrough, a hub having an open proximal end with a tapered cavity therein including a side wall tapered distally inwardly at a taper of from 4% to 8% said cavity having a diameter of less than about 3.85 mm at said open proximal end, and a distal end joined to said proximal end of said cannula so that said lumen is in fluid communication with said cavity, said needle assembly being connected to said barrel so that said elongated tip of said barrel engages said tapered cavity of said hub.

3. The syringe assembly of claim 2 wherein said side wall of said hub has a taper of about 6%.

4. The syringe assembly of claim 2 wherein said cavity of said hub has a diameter of about 3.7 mm at said open proximal end.

5. The syringe assembly of claim 2 further including an elongated needle shield removably connected to said hub so that said distal end of said cannula is in said needle shield.

6. The syringe assembly of claim 5 further including a package enclosing said syringe assembly.

7. The syringe assembly of claim 1 wherein said side wall of said tip has a taper of about 6%.

8. The syringe assembly of claim 1 wherein said tip has a diameter at its distal end of about 3.4 mm.

9. The syringe assembly of claim 1 further including a package enclosing said syringe.

10. The syringe assembly of claim 9 further including a needle assembly in said package, said needle assembly including a cannula having a proximal end, a distal end and a lumen therethrough, a hub having an open proximal end with a tapered cavity therein including a side wall tapered distally inwardly at a taper of from 4% to 8% said cavity having a diameter of less than about 3.85 mm at said open proximal end, said hub including a distal end joined to said proximal end of said cannula so that said lumen is in fluid communication with said cavity and a needle shield removably connected to said hub so that said distal end of said cannula is in said needle shield.

11. The syringe assembly of claim 10 wherein said needle assembly is aligned with and positioned adjacent to said syringe assembly in said package.

12. The syringe assembly of claim 11 wherein said syringe assembly is sterile.

13. The syringe assembly of claim 10 wherein said side wall of said tip has a taper of about 6% and said side wall of said hub has a taper of about 6%.

14. The syringe assembly of claim 1 wherein said stopper is made of elastomeric material selected from the group of natural rubber, synthetic rubber, thermoplastic elastomers and combinations thereof.

15. The syringe assembly of claim 1 wherein said plunger rod further includes weakening means for allowing said elongated body portion of said plunger rod to break if excessive amounts of force are applied to said proximal end of said elongated body portion.

16. The syringe assembly of claim 1 further including barrier means on said body portion for limiting the delivery volume of said syringe assembly by establishing the maximum proximal position of said locking element with respect to said elongate body portion.

17. The syringe assembly of claim 1 wherein said elongate body portion includes a longitudinal recess, said recess acting as a pathway for the longitudinal motion of said locking element relative to said elongate body portion between said stopper and said barrier means.

18. The syringe assembly of claim 17 wherein said longitudinal recess is v-shaped when viewed along the longitudinal axis of said body portion with the narrowest portion of said recess being closest to the center of the body portion.

19. The syringe assembly of claim 17 further including a delivery ledge in said recess for engaging said driving edge when said locking element is in about its furthest most distal position with respect to said recess for assuring distal motion of said locking element as said plunger moves distally along said barrel to expel fluid from said chamber.

20. The syringe assembly of claim 1 wherein said locking element includes a second proximally and outwardly facing locking barb and a second inwardly facing driving edge at said proximal portion of said element.

21. An operable syringe assembly comprising:
a barrel having an inside surface describing a chamber for retaining fluid, said barrel having an open proximal end and a distal end, and an elongated tip extending from said distal end having a passageway therethrough in fluid communication with said chamber, said tip having a diameter at its distal end of less than about 3.8 mm and a side wall tapered proximally outwardly at a taper of from 4% to 8%;
a plunger rod including an elongated body portion having a proximal end, a distal end, and a stopper at said distal end, said stopper being slidably positioned in fluid-tight engagement in said barrel, an elongated projection extending distally outwardly from said distal end of said plunger rod, said elongated projection being shaped to fit within said passageway of said elongated tip, said body portion extending outwardly from said open proximal end of said barrel;
means for preventing proximal motion of said plunger rod with respect to said barrel after distal motion of said stopper to expel fluid through said passageway; and
a needle assembly including a cannula having a proximal end, a distal end and a lumen therethrough, a hub having an open proximal end with a tapered cavity therein, said tapered cavity having a side wall tapered distally inwardly at a taper of from 4% to 8% said cavity having a diameter of less than about 3.85 mm at said open proximal end, said hub including a distal end joined to said proximal end of said cannula so that said lumen is in fluid communication with said cavity, said needle assembly being connected to said barrel so that said elongated tip of said barrel engages said tapered cavity of said hub.

22. The syringe assembly of claim 21 wherein said side wall of said tip has a taper of about 6% and said side wall of said hub has a taper of about 6%.

23. The syringe assembly of claim 21 further including a package enclosing said syringe assembly and a needle assembly, said needle assembly including a cannula having a proximal end, a distal end and a lumen therethrough, a hub having an open proximal end with a tapered cavity therein wherein said tapered cavity of said hub includes a side wall tapered distally inwardly at a taper of from 4% to 8%, said hub including a distal end joined to said proximal end of said cannula so that said lumen is in fluid communication with said cannula, said needle assembly further including an elongated needle shield removably connected to said hub so that said distal end of said cannula is in said needle shield.

24. The syringe assembly of claim 23 wherein said side wall of said tip has a taper of about 6% and said side wall of said hub has a taper of about 6%.

25. An operable syringe assembly comprising:

a barrel having an inside surface describing a chamber for retaining fluid, said barrel having an open proximal end and a distal end, and an elongated tip extending from said distal end having a passageway therethrough in fluid communication with said chamber, said tip having a side wall tapered proximally outwardly at a taper of about 6%;

a plunger rod including an elongated body portion having a proximal end, a distal end, and a stopper at said distal end, said stopper being slidably positioned in fluid-tight engagement in said barrel, an elongated projection extending distally outwardly from said distal end of said plunger rod, said elongated projection being shaped to fit within said passageway of said elongated tip, said body portion extending outwardly from said open proximal end of said barrel;

means for preventing proximal motion of said plunger rod with respect to said barrel after distal motion of said stopper to expel fluid through said passageway;

a needle assembly including a cannula having a proximal end, a distal end, and a lumen therethrough, a hub having an open proximal end with a tapered cavity therein including a side wall tapered distally inwardly at a taper of about 6% said cavity having a diameter of less than about 3.85 mm at said open proximal end, said hub including a distal end joined to said proximal end of said cannula so that said lumen is in fluid communication with said cavity and a needle shield removably connected to said hub so that said distal end of said cannula is in said needle shield; and a package enclosing said syringe assembly and said needle assembly.

26. The syringe assembly of claim 25 wherein said needle assembly is aligned with and positioned adjacent to said syringe assembly in said package.

27. The syringe assembly of claim 25 wherein said tip has a diameter at its distal end of about 3.4 mm.

28. The syringe assembly of claim 25 wherein said cavity of said hub has a diameter of about 3.7 mm at said open proximal end.

* * * * *